US010869869B2

(12) United States Patent
Laquerre et al.

(10) Patent No.: US 10,869,869 B2
(45) Date of Patent: Dec. 22, 2020

(54) METHOD OF ADJUVANT CANCER TREATMENT

(71) Applicant: Novartis AG, Basel (CH)

(72) Inventors: Sylvie Laquerre, King of Prussia, PA (US); Peter F. Lebowitz, Research Triangle Park, NC (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 16/664,978

(22) Filed: Oct. 28, 2019

(65) Prior Publication Data

US 2020/0054641 A1 Feb. 20, 2020

Related U.S. Application Data

(63) Continuation of application No. 16/056,702, filed on Aug. 7, 2018, now abandoned, which is a continuation of application No. 15/479,663, filed on Apr. 5, 2017, now abandoned, which is a continuation of application No. 14/422,182, filed as application No. PCT/US2013/057432 on Aug. 30, 2013, now abandoned.

(60) Provisional application No. 61/696,375, filed on Sep. 4, 2012.

(51) Int. Cl.
*A61K 31/506* (2006.01)
*A61K 31/519* (2006.01)

(52) U.S. Cl.
CPC .......... *A61K 31/519* (2013.01); *A61K 31/506* (2013.01)

(58) Field of Classification Search
CPC .......................... A61K 31/519; A61K 31/506
See application file for complete search history.

(56) References Cited

FOREIGN PATENT DOCUMENTS

WO 2011/047238 4/2011
WO 2012/095505 A1 7/2012

OTHER PUBLICATIONS

Michnin A.E. et al., "Malignant melanoma of the skin: search for standards of treatment", Practical Oncology No. 4 (8), pp. 69-72, 2001. English translation of the relevant parts.
Atefi et al., "Reversing Melanoma Cross-Resistance to BRAF and MEK Inhibitors by Co-Targeting the AKT/mTOR Pathway", PLoS One, 2011, vol. 6, No. 12, e28973.
Batchelor, J.S., "MEK and BRAF Therapy Combo Promising for Advanced Melanoma", Published online Jun. 5, 2011, (URL: http://www.onclive.com/conference-coverage/asco-2011/MEK-and-BRAF-Therapy-Combo-Promisng-for-Advanced-Melanoma).
Nfante et al. "Hase I/ii study to assess safety, pharmacokinetics, and efficacy of oral MEK 1/2 inhibitor GSK1120212 (GSK212) dosed in combination with the oral BRAF inhibitor GSK2118436 (GSK436)", 2011 ASCO Annual Meeting, Journal of Clinical Oncology, 2011 vol. 29, Supplement, Abstract CRA9503, Found online at (http://meetinglibrary.asco.org/content/80485-102).
Journal of Translational Medicine, May 2012, 10(85), p. 1-9.
"Dabrafenib/Trametinib Combination Receives CHMP Recommendation for the Adjuvant Treatment of BRAF V600 Mutation-Positive Melanoma", ASCO Post, http://www.ascopost.com/News/59122.
"Adjuvant Vemurafenib in Resected BRAF V600-Mutant Melanoma", ASCO Post, http://www.ascopost.com/News/58601.

*Primary Examiner* — San Ming R Hui
(74) *Attorney, Agent, or Firm* — Gregory Houghton

(57) ABSTRACT

The present invention provides a method of providing adjuvant treatment to a human patient which comprises administering to such a patient therapeutically effective doses of dabrafenib and trametinib for a time period sufficient to increase relapse-free survival (RFS).

3 Claims, No Drawings

METHOD OF ADJUVANT CANCER TREATMENT

BACKGROUND OF THE INVENTION

This invention relates to a method of treating subjects after complete resection of cutaneous melanoma.

Cutaneous melanoma is the most aggressive form of all skin cancers. Although it represents only 4% of all cancers, its incidence is continuing to rise in the world at a rate exceeding all other cancers (Jemal A, Siegel R, Ward E et al. Cancer statistics, 2007. CA Cancer J Clin 2007; 57: 43-66). Worldwide it is expected that approximately 132,000 people will be diagnosed with melanoma each year and approximately 37,000 people are expected to die of the disease annually (World Health Organization (WHO). Skin cancers. In *Ultraviolet radiation and the INTERSUN Programme*. Retrieved 7 Feb. 2012).

Surgical resection is the treatment of choice for localized melanoma and frequently results in cures for early stage (I and II) disease, with a 90% long term (10-year) survival rate for stage I disease Balch et al., Final Version of 2009 AJCC Melanoma Staging and Classification. J Clin Oncol. 2009; 27:6199-6206). However, patients with lymph node involvement ≥1 mm, including those detected only by sentinel lymph node biopsy, are at high risk of both local and distant relapse after definitive surgery due to the frequent presence of distant micrometastatic disease at presentation (Kirkwood et al. High-dose interferon alfa-2b significantly prolongs relapse-free and overall survival compared with the GM2-KLH/QS-21 vaccine in patients with resected stage II-III melanoma: Results of Intergroup Trial E1694/S9512/C509801. *J Clin Oncol* 2001; 19: 2370-80; Van Akkooi et al. Long-term follow-up of patients with minimal sentinel node tumor burden (<0.1 mm) according to Rotterdam criteria: A study of the EORTC Melanoma Group. J Clin Oncol, 2009; 27:15s (suppl abstr 9005). Approximately half of these patients will ultimately die of metastatic disease (Markovic S N, et al. Malignant melanoma in the 21st century, part 2: staging, prognosis and treatment. Mayo Clin. Proc. 2007; 82: 490-513), and the morbidity from uncontrolled relapses is also considerable. Thus there is a need for effective adjuvant therapy for high-risk patients to prevent disease relapse after surgical resection of the primary tumor.

Although significant progress has been made recently with new treatments for metastatic melanoma, therapeutic options in the adjuvant setting remain limited. Many agents have been evaluated as potential therapies for the adjuvant treatment of melanoma however almost all have demonstrated little or no benefit (Schuchter L. Adjuvant Interferon Therapy for Melanoma: High-Dose, Low-Dose, No Dose, Which Dose? J Clin Oncol 2004; 22:7-10). The National Comprehensive Cancer Network (NCCN) treatment guidelines for melanoma recommend clinical trials, observation and interferon as the three therapy options for the adjuvant treatment of melanoma with clinical trials as the preference (National Comprehensive Cancer Network (NCCN). NCCN Clinical Practice Guidelines in Oncology: Melanoma. NCCN, Ft. Washington, Pa.; 2012). Although high-dose interferon is currently the only approved therapy for the adjuvant treatment of melanoma it is not widely accepted as the standard of care. Increasing evidence surrounding a questionable survival benefit, a high incidence of serious toxicities, and negligible benefit for patients with bulkier disease makes it an unattractive therapy for most patients and clinicians (Schuchter, 2004). Thus, there is a need for more effective therapies with an acceptable safety profile in the adjuvant setting.

SUMMARY OF THE INVENTION

The present invention provides a method of providing adjuvant treatment to a patient with a prior diagnosis of melanoma which has been resected, which comprises administering to such a patient therapeutically effective doses of dabrafenib and trametinib for a time period sufficient to increase relapse-free survival (RFS).

According to one embodiment of the invention, there is provided a method of increasing relapse-free survival (RFS) after resection of melanoma, which comprises administration of a) dabrafenib and b) trametinib.

According to another embodiment of the invention, there is provided the combination of dabrafenib and trametinib for use in increasing relapse-free survival (RFS) after resection of melanoma.

According to another embodiment of the invention, the patient has a prior diagnosis of stage III melanoma which primary tumor has been resected.

According to another embodiment of the invention, the patient has a prior diagnosis of BRAF V600 mutation-positive melanoma which has been resected. According to another embodiment, the patient has stage III BRAF V600-mutation positive melanoma which has been resected.

DETAILED DESCRIPTION OF THE INVENTION

The RAS/RAF/MEK/ERK pathway (i.e., the MAP kinase pathway) is a critical proliferation pathway in many human cancers, including melanoma. Oncogenic mutations in BRAF signal through MEK1 and MEK2, and occurrence of this is an early event. This study will evaluate the combination of two small-molecules, oral agents, dabrafenib and trametinib. Dabrafenib is a potent and selective RAF kinase inhibitor of human wild type BRAF and CRAF enzymes as well as the mutant forms BRAFV600E, BRAFV600K and BRAFV600D. The mode of action of dabrafenib is consistent with competitive inhibition of adenosine triphosphate (ATP) binding. By contrast, trametinib is a reversible, highly selective, allosteric Inhibitor of MEK1 and MEK2. Trametinib is non-competitive towards ATP and inhibits both MEK activation and kinase activity. Because BRAF and MEK are in the same pathway, and because MEK is a substrate of activated BRAF and other kinases that can be activated in presence of BRAF inhibition, inhibiting both proteins simultaneously rather than individually could provide more effective pathway inhibition and also decrease the likelihood of developing resistance.

Preliminary clinical experience, along with data generated in cell line, mouse xenograft, and rat safety models with BRAF and MEK inhibitor combinations suggest enhanced effects on efficacy and reduced toxicity such as reduction of proliferative skin lesions or reduction of growth stimulation of cells containing RAS mutations compared to treatment with a BRAF inhibitor alone.

The term "dabrafenib" as used herein means the B-Raf inhibitor represented by the structure of formula (II):

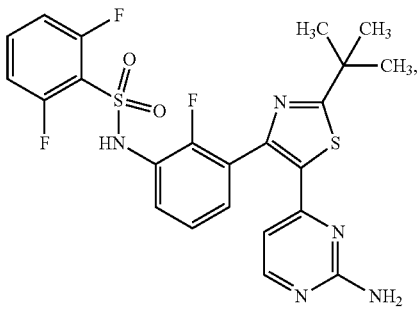 [SMILES: CC(C)(C)c1nc(-c2cccc(NS(=O)(=O)c3c(F)cccc3F)c2F)c(-c2ccnc(N)n2)s1]

or a pharmaceutically acceptable salt thereof.

Dabrafenib is preferably administered as its mesylate salt as N-{3-[5-(2-Amino-4-pyrimidinyl)-2-(1,1-dimethylethyl)-1,3-thiazol-4-yl]-2-fluorophenyl}-2,6-difluorobenzenesulfonamide methanesulfonate.

Dabrafenib is disclosed and claimed, along with pharmaceutically acceptable salts thereof, as being useful as an inhibitor of BRaf activity, particularly in the treatment of cancer, in PCT patent publication WO2009/137391. Dabrafenib is embodied by Examples 58a through 58e of the application.

Dabrafenib is a potent and selective RAF kinase inhibitor of human wild type BRAF and CRAF enzymes as well as the mutant forms BRAFV600E, BRAFV600K and BRAFV600D. Accordingly, one embodiment of the invention includes adjuvant treatment of patients having BRAFV600E, BRAFV600K, and/or BRAFV600D mutation-positive melanoma which has been resected.

The term "trametinib" as used herein means the MEK inhibitor represented by the structure of formula (I):

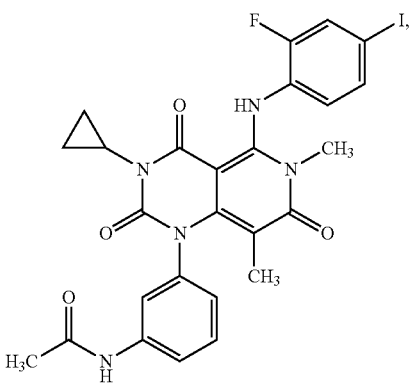 [SMILES: CC(=O)Nc1cccc(-n2c(=O)n(C3CC3)c(=O)c3c(Nc4ccc(I)cc4F)n(C)c(=O)c(C)c32)c1]

or a pharmaceutically acceptable salt or solvate thereof. Trametinib is preferably administered as a solvate in the form of N-{3-[3-cyclopropyl-5-(2-fluoro-4-iodo-phenylamino)6,8-dimethyl-2,4,7-trioxo-3,4,6,7-tetrahydro-2H-pyrido[4,3-d]pyrimidin-1-yl]phenyl}acetamide dimethyl sulfoxide (solvate). Depending on naming convention, the compound of formula (I) may also properly be referred to as N-{3-[3-cyclopropyl-5-[(2-fluoro-4-iodophenyl)amino]-6,8-dimethyl-2,4,7-trioxo-3,4,6,7-tetrahydropyrido[4,3-d]pyrimidin-1 (2H)-yl]phenyl}acetamide.

Trametinib is disclosed and claimed, along with pharmaceutically acceptable salts thereof, and also as solvates thereof, as being useful as an inhibitor of MEK activity, particularly in treatment of cancer, in WO 2005/121142. Trametinib can be prepared as described in WO 2005/121142.

Suitably, trametinib is in the form of a dimethyl sulfoxide solvate. Suitably, trametinib is in the form of a sodium salt. Suitably, trametinib is in the form of a solvate selected from: hydrate, acetic acid, ethanol, nitromethane, chlorobenzene, 1-pentancol, isopropyl alcohol, ethylene glycol and 3-methyl-1-butanol. These solvates and salt forms can be prepared by one of skill in the art from the description in WO 2005/121142.

As used herein, "resection" is understood to mean surgical removal of malignant tissue characteristic of melanoma from a human patient. According to one embodiment, resection shall be understood to mean removal of malignant tissue such that the presence of remaining malignant tissue within said patient is undetectable with available methods. According to another embodiment of the invention, resection shall be understood to mean removal of melanoma such that the presence of remaining melanoma with said patient is undetectable.

As used herein, "treatment" or "adjuvant treatment" is understood to refer to the administration of a drug or drugs to a patient after surgical resection of one or more cancerous tumors, where all detectable and resectable disease (e.g. cancer) has been removed from the patient, but where there remains a statistical risk of relapse due to occult disease, for the purpose of diminishing the likelihood or the severity of reoccurrence or the disease, or to delay the onset of the biological manifestation of the reoccurrence of the disease.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

While it is possible that, for use in therapy, dabrafenib and trametinib may be administered as the raw chemical, it is possible to present the active ingredient as a pharmaceutical composition. Accordingly, the invention further provides pharmaceutical compositions, which include dabrafenib and/or trametinib, and one or more pharmaceutically acceptable carriers, diluents, or excipients. The carrier(s), diluent(s) or excipient(s) must be acceptable in the sense of being compatible with the other ingredients of the formulation, capable of pharmaceutical formulation, and not deleterious to the recipient thereof. In accordance with another aspect of the invention there is also provided a process for the preparation of a pharmaceutical composition including admixing dabrafenib and/or trametinib, with one or more pharmaceutically acceptable carriers, diluents or excipients. Such elements of the pharmaceutical compositions utilized may be presented in separate pharmaceutical combinations or formulated together in one pharmaceutical composition. Accordingly, the invention further provides a combination of pharmaceutical compositions one of which includes trametinib and one or more pharmaceutically acceptable carriers, diluents, or excipients and a pharmaceutical composition containing dabrafenib and one or more pharmaceutically acceptable carriers, diluents, or excipients.

Dabrafenib and/or trametinib may be administered by any appropriate route. Suitable routes include oral, rectal, nasal, topical (including buccal and sublingual), vaginal, and parenteral (including subcutaneous, intramuscular, intravenous, intradermal, intrathecal, and epidural). It will be appreciated that the preferred route may vary with, for example, the condition of the recipient of the combination and the cancer to be treated. It will also be appreciated that each of the agents administered may be administered by the same or different routes and that the compounds may be compounded together in a pharmaceutical composition.

Dabrafenib and trametinib may be employed in combination in accordance with the invention by administration simultaneously in a unitary pharmaceutical composition including both compounds. Alternatively, the combination may be administered separately in separate pharmaceutical compositions, each including one of the dabrafenib and trametinib in a sequential manner wherein, for example, trametinib or dabrafenib is administered first and the other second. Such sequential administration may be close in time (eg. simultaneously) or remote in time. Furthermore, it does not matter if the compounds are administered in the same dosage form, e.g. one compound may be administered topically and the other compound may be administered orally. Suitably, both compounds are administered orally. Thus in one embodiment, one or more doses of trametinib are administered simultaneously or separately with one or more doses of dabrafenib.

Suitably, the amount of trametinib (based on weight of unsalted/unsolvated amount) administered as part of the combination according to the present invention will be an amount selected from about 0.125 mg to about 10 mg; suitably, the amount will be selected from about 0.25 mg to about 9 mg; suitably, the amount will be selected from about 0.25 mg to about 8 mg; suitably, the amount will be selected from about 0.5 mg to about 8 mg; suitably, the amount will be selected from about 0.5 mg to about 7 mg; suitably, the amount will be selected from about 1 mg to about 7 mg; suitably, the amount will be about 5 mg. Accordingly, the amount of trametinib administered as part of the combination according to the present invention will be an amount selected from about 0.125 mg to about 10 mg. For example, the amount of trametinib administered as part of the combination according to the present invention can be 0.125 mg, 0.25 mg, 0.5 mg, 0.75 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg.

Suitably, the amount of dabrafenib (based on weight of unsalted/unsolvated amount) administered as part of the combination according to the present invention will be an amount selected from about 10 mg to about 600 mg. Suitably, the amount will be selected from about 30 mg to about 300 mg; suitably, the amount will be selected from about 30 mg to about 280 mg; suitably, the amount will be selected from about 40 mg to about 260 mg; suitably, the amount will be selected from about 60 mg to about 240 mg; suitably, the amount will be selected from about 80 mg to about 220 mg; suitably, the amount will be selected from about 90 mg to about 210 mg; suitably, the amount will be selected from about 100 mg to about 200 mg, suitably, the amount will be selected from about 110 mg to about 190 mg, suitably, the amount will be selected from about 120 mg to about 180 mg, suitably, the amount will be selected from about 130 mg to about 170 mg, suitably, the amount will be selected from about 140 mg to about 160 mg, suitably, the amount will be 150 mg. Accordingly, the amount of dabrafenib administered as part of the combination according to the present invention will be an amount selected from about 10 mg to about 300 mg. For example, the amount of dabrafenib administered as part of the combination according to the present invention is suitably selected from 10 mg, 20 mg, 30 mg, 40 mg, 50 mg, 60 mg, 70 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg and 300 mg. Suitably, the selected amount of dabrafenib is administered from 1 to 4 times a day. Suitably, the selected amount of dabrafenib is administered twice a day. Suitably, dabrafenib is administered at an amount of 150 mg twice a day. Suitably, the selected amount of dabrafenib is administered once a day.

In another embodiment, the combination of the invention may be employed with other therapeutic methods of cancer treatment. In particular, in anti-neoplastic therapy, combination therapy with other chemotherapeutic, hormonal, antibody agents as well as surgical and/or radiation treatments other than those mentioned above are envisaged. Combination therapies according to the present invention thus include the administration of trametinib and dabrafenib as well as optional use of other therapeutic agents including other anti-neoplastic agents. Such combination of agents may be administered together or separately and, when administered separately this may occur simultaneously or sequentially in any order, both close and remote in time. In one embodiment, the pharmaceutical combination includes trametinib and dabrafenib, and optionally at least one additional anti-neoplastic agent.

BACKGROUND

Cutaneous melanoma is the most aggressive form of all skin cancers. Although it represents only 4% of all cancers, its incidence is continuing to rise in the world at a rate exceeding all other cancers [Jemal, 2007]. Worldwide it is expected that approximately 132,000 people will be diagnosed with melanoma each year and approximately 37,000 people are expected to die of the disease annually [WHO, 2012].

Surgical resection is the treatment of choice for localized melanoma and frequently results in cures for early stage (I and II) disease, with a 90% long term (10-year) survival rate for stage I disease [Balch, 2009]. However, patients with lymph node involvement ≥1 mm, including those detected only by sentinel lymph node biopsy, are at high risk of both local and distant relapse after definitive surgery due to the frequent presence of distant micrometastatic disease at presentation [Kirkwood, 2001; Van Akkooi, 2009]. Approximately half of these patients will ultimately die of metastatic disease [Markovic, 2007], and the morbidity from uncontrolled relapses is also considerable. Thus there is a need for effective adjuvant therapy for high-risk patients to prevent disease relapse after surgical resection of the primary tumor.

Although significant progress has been made recently with new treatments for metastatic melanoma, therapeutic options in the adjuvant setting remain limited. Many agents have been evaluated as potential therapies for the adjuvant treatment of melanoma however almost all have demonstrated little or no benefit [Schuchter, 2004]. The National Comprehensive Cancer Network (NCCN) treatment guidelines for melanoma recommend clinical trials, observation and interferon as the three therapy options for the adjuvant treatment of melanoma with clinical trials as the preference [NCCN, 2012]. Although high-dose interferon is currently the only approved therapy for the adjuvant treatment of melanoma it is not widely accepted as the standard of care. Increasing evidence surrounding a questionable survival benefit, a high incidence of serious toxicities, and negligible benefit for patients with bulkier disease makes it an unattractive therapy for most patients and clinicians [Schuchter, 2004]. Thus there is a need for more effective therapies with an acceptable safety profile in the adjuvant setting.

Study Design

This is a two-arm, randomized, double-blind Phase III study of dabrafenib in combination with trametinib versus two placebos in the adjuvant treatment of melanoma after surgical resection. Patients with completely resected, histologically confirmed, BRAF V600E/K mutation-positive, high-risk [Stage IIIa (lymph node metastasis >1 mm), IIIb or IIIc] cutaneous melanoma will be screened for eligibility. Approximately 852 subjects will be randomized in a 1:1 ratio to receive either dabrafenib (150 mg BID) and trametinib (2 mg once daily) combination therapy or two placebos for each for 12 months.

Doses of study treatment may be modified and/or interrupted for management of toxicities associated with study treatment.

The benefit of the dabrafenib/trametinib combination compared to placebos will be evaluated through the primary endpoint of investigator-assessed relapse free survival (RFS). Crossover is not permitted.

Subjects in both arms will receive treatment for 12 months or until disease recurrence, death, unacceptable toxicity, or withdrawal of consent. Subjects will be followed for disease recurrence and survival during and after the treatment period.

The primary objective for this study is to evaluate the efficacy of dabrafenib and trametinib combination therapy compared to two placebos with respect to relapse-free survival (RFS) in patients with completely resected, histologically confirmed, BRAF V600E/K high-risk, stage III cutaneous melanoma. Secondary efficacy objectives include:

To evaluate the overall survival (OS) of dabrafenib and trametinib combination therapy compared to placebo
To assess distant metastasis-free survival (DMFS)
To assess freedom from relapse (FFR)

Discussion of Design

The ultimate goal of adjuvant therapy is to improve the cure rate after surgery through eradication of occult micro-metastatic disease. Notable successes have been achieved in oncology when highly effective therapies were available for advanced stage disease (e.g., breast cancer, Hodgkin's and non-Hodgkin's lymphoma, embryonal tumors, osteosarcoma). High-risk, resected BRAF V600E/K mutation positive melanoma represents another attractive setting for testing this paradigm since: 1) the population is at high risk for relapse and death without further therapy; 2) the BRAF/MEK combination is both highly effective and can be targeted to the population most likely to benefit, and 3) the combination of dabrafenib and trametinib should be at least as well tolerated as cytotoxic chemotherapy or high-dose interferon and thus have acceptable risk:benefit if the study objectives are met.

This study is designed to compare dabrafenib and trametinib in combination versus two placebos with regard to RFS, which is a direct measurement of anti-tumor effect. RFS was selected as the primary endpoint based upon historical precedent (peginterferon alfa-2b, Sylatron) and because it will not be subject to confounding from subsequent therapy, as would OS. Since relapses are accompanied by considerable disease- and treatment-related morbidity, RFS is a true measure of patient benefit.

Subject Selection and Discontinuation/Completion Criteria

Approximately 852 subjects will be randomized, 1:1 to combination therapy (n=426) and to placebos (n=426).

Inclusion Criteria

Subjects eligible for enrolment in the study must meet all of the following criteria:

1. Is ≥18 years of age.
2. Has signed written informed consent.
3. Completely resected histologically confirmed high-risk [Stage IIIa (LN metastasis >1 mm), IIIb or IIIc] cutaneous melanoma determined to be V600E/K mutation positive using the bioMerieux (bMX) investigational use only (IUO) THxID BRAF Assay (IDE: G120011). The testing will be conducted by a central reference laboratory. Patients presenting with initial resectable lymph node recurrence after a diagnosis of Stage I or II melanoma are eligible.
4. Must be surgically rendered free of disease no more than 12 weeks before randomization.
5. Recovered from definitive surgery (e.g. no uncontrolled wound infections or indwelling drains).
6. Able to swallow and retain oral medication and must not have any clinically significant gastrointestinal abnormalities that may alter absorption such as malabsorption syndrome or major resection of the stomach or bowels.
7. Eastern Cooperative Oncology Group (ECOG) Performance Status of 0-1.
8. Must have adequate organ function as defined in Table 1:

TABLE 1

Definitions for Adequate Baseline Organ Function

| System | Laboratory Values |
|---|---|
| Hematologic | |
| ANC | ≥1.2 × 10$^9$/L |
| Hemoglobin | ≥9 g/dL |
| Platelet count | ≥100 × 10$^9$/L |
| PT/INR$^a$ and PTT | ≤1.5 × ULN |
| Hepatic | |
| Albumin | ≥2.5 g/dL |
| Total bilirubin | ≥1.5 × ULN |
| AST and ALT | ≥2.5 × ULN |
| Renal | |
| Serum creatinine$^b$ | ≤1.5 mg/dL |
| Cardiac | |
| Left Ventricular Ejection fraction (LVEF)$^c$ | ≥LLN by ECHO |

Abbreviations: ALT = alanine transaminase; ANC = absolute neutrophil count; AST = aspartate aminotransferase; INR = international normalized ratio; LLN = lower limit of normal; PT = prothrombin time; PTT = partial thromboplastin time; ULN = upper limit of normal.
$^a$Subjects receiving anticoagulation treatment may be allowed to participate with INR established within the therapeutic range prior to randomization.
$^b$If serum creatinine is >1.5 mg/dL, calculate creatinine clearance using standard Cockcroft-Gault formula. Creatinine clearance must be ≥50 mL/min to be eligible.
$^c$ECHO scans must be used throughout the study 9. Women of childbearing potential must have a negative serum pregnancy test within 7 days of first dose of study treatment and agree to use effective contraception, from 14 days prior to randomization, throughout the treatment period and for 4 months after the last dose of study treatment.

10. French subjects: In France, a subject will be eligible for inclusion in this study only if either affiliated to or a beneficiary of a social security category.

Exclusion Criteria

Subjects meeting any of the following criteria must not be enrolled in the study:

1. Known mucosal or ocular melanoma or the presence of unresectable in-transit metastases.
2. Evidence of distant metastatic disease on screening evaluation.
3. Prior systemic anti-cancer treatment (chemotherapy, immunotherapy, biologic therapy, vaccine therapy, or investigational treatment) and radiotherapy for melanoma. Prior surgery for melanoma is allowed.
4. Taken an investigational drug within 28 days or 5 half-lives, whichever is longer, prior to randomization.
5. Current or expected use of a prohibited medication.
6. Known immediate or delayed hypersensitivity reaction or idiosyncrasy to drugs chemically related to the study treatments, their excipients, and/or dimethyl sulfoxide (DMSO).
7. Known Human Immunodeficiency Virus (HIV).
8. A history of known glucose-6-phosphate dehydrogenase (G6PD) deficiency.
9. History of another malignancy including melanoma or a concurrent malignancy except as noted below:
    Exceptions: Subjects who have been disease-free for 5 years, or subjects with a history of completely resected non-melanoma skin cancer or successfully treated in situ carcinoma are eligible, for example cervical cancer in situ, atypical melanocytic hyperplasia or melanoma in situ, multiple primary melanomas, or other malignancies for which the patient has been disease free for >5 years.
10. A history or evidence of cardiovascular risk including any of the following:
    a. A QT interval corrected for heart rate using the Bazett's formula (QTcB) ≥480 msec;
    b. A history or evidence of current clinically significant uncontrolled arrhythmias;
    c. A history of acute coronary syndromes (including myocardial infarction or unstable angina), coronary angioplasty, or stenting within 6 months prior to randomization
    d. A history or evidence of current ≥Class II congestive heart failure as defined by the New York Heart Association (NYHA) guidelines
    e. Patients with intra-cardiac defibrillators or permanent pacemakers.
    f. Abnormal cardiac valve morphology (≥grade 2) documented by echocardiogram (subjects with grade 1 abnormalities [i.e., mild regurgitation/stenosis] can be entered on study). Subjects with moderate valvular thickening should not be entered on study.
    g. Treatment refractory hypertension defined as a blood pressure of systolic >140 mm Hg and/or diastolic >90 mm Hg which cannot be controlled by anti-hypertensive therapy
11. A history or current evidence/risk of retinal vein occlusion (RVO) or central serous retinopathy (CSR) including:
    a. Presence of predisposing factors to RVO or CSR (e.g., uncontrolled glaucoma or ocular hypertension, uncontrolled hypertension, uncontrolled diabetes mellitus, or a history of hyperviscosity or hypercoagulability syndromes); or
    b. Visible retinal pathology as assessed by ophthalmic examination that is considered a risk factor for RVO or CSR such as:
        i. Evidence of new optic disc cupping;
        ii. Evidence of new visual field defects on automated perimetry;
        iii. Intraocular pressure >21 mm Hg as measured by tonography.
12. Interstitial lung disease or pneumonitis.
13. Any serious or unstable pre-existing medical conditions (aside from malignancy exceptions specified above), psychiatric disorders, or other conditions that, in the opinion of the investigator, could interfere with the subject's safety, obtaining informed consent, or compliance with study procedures.
14. Pregnant or nursing females.

Permanent Discontinuation from Study Treatment and Subject Completion Criteria

Subjects will receive study treatments for twelve months or until disease recurrence.

During the protocol defined treatment period study treatment(s) may be permanently discontinued for the following reasons:
    death
    unacceptable adverse event, including meeting stopping criteria for liver chemistry and/or for hematologic and other non-hematologic toxicity.
    deviation(s) from the protocol
    request of the subject or proxy
    investigator's discretion
    subject is lost to follow-up
    study is closed or terminated.

If disease recurs prior to the completion of the 12 month treatment period, study treatment should be discontinued and follow-up assessments should be conducted. All subjects who permanently discontinue study treatment without evidence of disease recurrence will also be followed for disease recurrence according to the protocol schedule until:
    Withdrawal of consent
    Death, or
    Study completion Follow-up will continue for all subjects including those with disease recurrence, until the study is considered to be complete after which all protocol-required assessments and procedures will be discontinued.

A subject will be considered to have completed the study if the subject dies during the study treatment or follow-up period. A subject will be considered to have withdrawn from the study if the subject has not died and is lost to follow-up, has withdrawn consent, at the investigator's discretion is no longer being followed or if the study is closed/terminated. Subjects who are ongoing at the time the study is closed/terminated will be considered to have completed the study.

Study Assessments

Subjects will be assessed with computed tomography (CT) or magnetic resonance imaging (MRI) at Screening and during treatment and the post-treatment follow-up period. Clinical assessments including vital signs and physical examinations, 12-lead ECG, ECHO, eye exams, chemistry and hematology laboratory values, and AEs will be monitored and evaluated. Subjects will also be followed for survival.

Study Treatment

Subjects will be identified by a unique subject number that will remain consistent for the duration of the study.

Upon completion of all the required screening assessments, eligible subjects will be registered into the GSK interactive voice response system (IVRS), by the investigator or authorized site staff.

Randomization will be done centrally using a randomization schedule generated by the GSK Biostatistical Department, which will assign subjects in a 1:1 ratio to:
- dabrafenib and trametinib combination therapy;
- dabrafenib and trametinib placebos Blinding Study treatment will be double-blinded.

Dose Modification Guidelines

The severity of adverse events will be graded utilizing the National Cancer Institute (NCI) CTCAE, version 4.0. Supportive and dose modification guidelines will be provided to investigators in event of adverse or serious adverse event(s), including drug termination and re-starting criteria. Drug-drug interaction and overdose information will also be provided to the investigators.

Endpoints

The primary efficacy endpoint of this study is relapse free survival (RFS) which is defined as the time from randomization to disease recurrence or death from any cause. Recurrence of or death from the same cancer and all deaths from other causes are events. Treatment emergent malignancies (excluding second melanomas) will not be considered as events, and loss to follow-up is censored.

The secondary efficacy endpoints of this study are:
- Overall Survival (OS) defined as the interval from randomization to the date of death, irrespective of the cause of death; patients still alive will be censored at the date of the last contact.
- Distant metastasis-free survival (DMFS), defined as the interval from randomization to the date of first distant metastasis or date of death, whichever occurs first. Patients alive and without distant metastasis are censored at the date of last assessment.
- Freedom from relapse (FFR), defined as interval from randomization to local or distant recurrence or new melanoma primary, with censoring of patients dying from causes other than melanoma or treatment-related toxicity at the date of death. Incidence of new melanoma will not be considered as an event. Patients alive without recurrence or with second primary cancers will be censored at the date of last assessment.

What is claimed is:

1. A method for providing adjuvant treatment to a patient with a prior diagnosis of melanoma which has been resected, comprising the steps of:
   a) administering to said patient therapeutically effective doses of dabrafenib and trametinib, wherein said dabrafenib is administered at an amount of 150 mg twice a day and said trametinib is administered at an amount of 2 mg once daily; and
   b) increasing relapse-free (RFS) of said patient after resection of said melanoma.

2. The method of claim 1, wherein said patient has a prior diagnosis of stage III melanoma, which has been resected.

3. The method of claim 1, wherein said patient has a prior diagnosis of BRAF V600 mutation-positive melanoma, which has been resected.

* * * * *